March 29, 1955 J. D. BROWNELL Plant Pat. 1,372
ROSE PLANT
Filed April 13, 1954
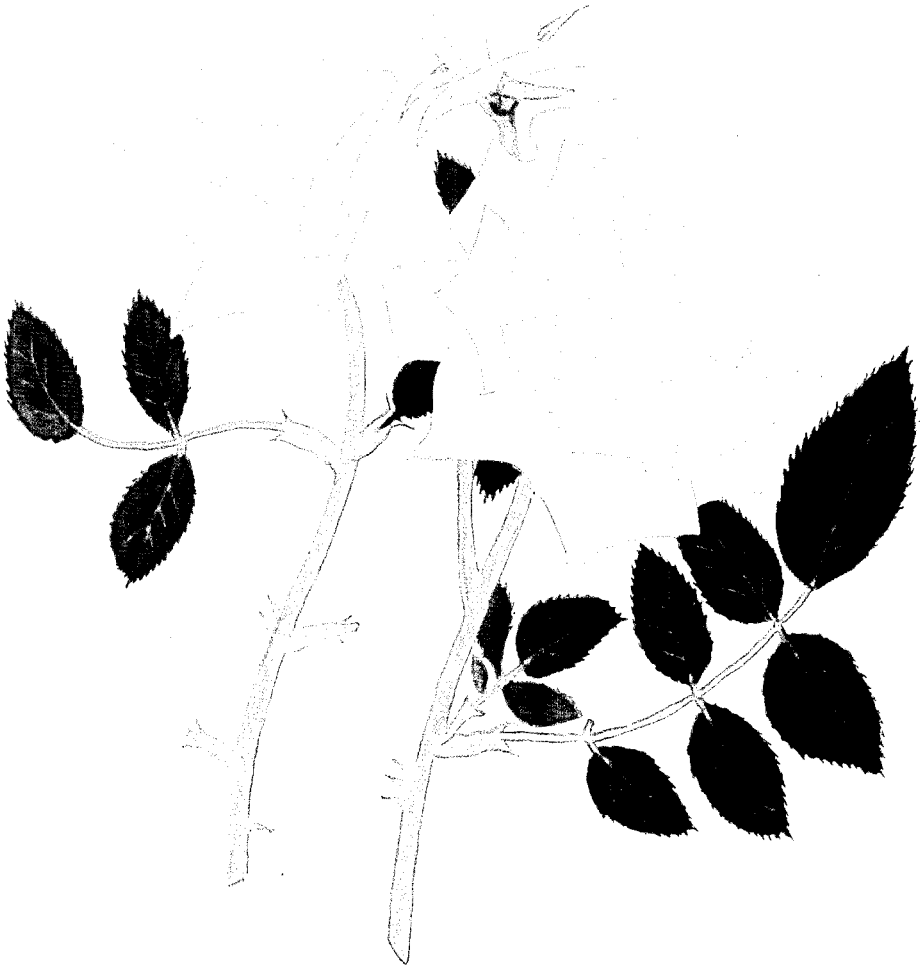
INVENTOR.
Josephine D. Brownell.

United States Patent Office

Plant Pat. 1,372

Patented Mar. 29, 1955

1,372

ROSE PLANT

Josephine D. Brownell, Little Compton, R. I.

Application April 13, 1954, Serial No. 423,008

1 Claim. (Cl. 47—61)

My invention relates to roses and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by selection of variety variations and by cross pollenation, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the northern United States;

The light yellow shading inward to light pink (ordinary dictionary definition) of its petals, in combination with the unique brilliance thereof and their tendency to hold these colors under exposure;

The novelty and variation within certain definite limits of the form of the bloom, its character of holding that form for a long time and the petallage of the flowers;

Its character of fragrance;

Its unusual abundance of flowers, notable after early bloom time and until frost;

The intensity of its remontant and everblooming or reblooming character;

Its character of ascending in height by recurrent branching and progressively longer stems from the base.

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

And especially its characteristic of partial freedom from premature defoliation by blackspot in that, on the average the foliage is a culture medium for blackspot under normal conditions to the extent of about one-half that of the average rose varieties in commerce without any cultural control.

In the accompanying drawing forming a part of this specification I have shown my new rose in its natural colors, that is, as near as is possible to do so artificially.

My new rose is otherwise described as follows:

ESSENTIAL INFORMATION

*Type*

Hybrid tea, *Rosa wichuraiana* hybrid, dwarf hybrid tea type ascending under normal conditions to about five feet in height after two years of growth, for garden display, cut flower and forcing or growing under glass.

*Class*

Hybrid tea crossed with *Rosa wichuraiana*, further restricted by originator to include only those varieties that can survive moderately low sub-zero temperatures.

*Breeding*

This variety was produced and bred by me and under my direction by propagation, selection and cross pollenation.

It came into being as a seedling grown from a seed born on a plant of Curly Pink Plant Patent No. 842 and the pollen parent was Shades of Autumn Plant Patent No. 542.

The pollenation that fertilized the seed that grew into my new rose, as well as the two previous pollenations that produced its two parents, were directed by me and were performed by emasculating flowers and placing thereon a bag protecting from self and foreign pollen. These bags were later removed and the flowers were hand pollenated with a camel's hair brush and the bags immediately replaced. The date of the pollenation of my new rose was July 17, 1949.[1] The seed was planted for me and under my direction on December 22, 1949, and the date of the first flower was July 28, 1950.

The plant and flower seemed to me to be of unusual merit and I have since made and directed extensive propagations and tests thereof.

Plants of this variety budded from this seedling on to *Rosa multiflora* root stocks, have after being exposed to moderate subzero temperatures, survived and bloomed normally the following season in the hybrid tea manner. The variety has been propagated by budding at Little Compton, Rhode Island, in the months of July and August 1951 and the characters have successively reproduced, true to the original seedling.

FLOWER

*Habit*

It blooms out of doors in Little Compton, beginning about three days prior to the average beginning time of commercial hybrid teas and continues relative to growth of the plant until frost.

*Flowers borne*

Often one and frequently two or three and occasionally more on each stem, in the usual hybrid tea type of cluster. And frequently on unusually large stems in open clusters in the manner of floribundas, or more free flowering types; and later in the season branches frequently grow therefrom with terminal flowers.

All of the foregoing bloom expression usually obtains the first year after budding, on maidens and on two year old plants the first growing season after being transplanted.

The pedicels and peduncles are medium in diameter and medium in length, erect, stiff, almost smooth, free from large prickles and bristles. Stems are long, diameter medium and moderately stiff and rigid.

*Quantity of bloom*

Free, being cumulative in quantity from year to year as the plant increases in size, flowering through the summer and fall.

*Fragrance*

Distinctive, pleasing china tea in combination with that of *Rosa wichuraiana*, under favorable environment.

*Bud*

Neck normal as described, opens well, being little to not at all affected by hot or wet weather or both, as to color and form, except at very high temperatures the color is less intense and the form of the petals is less recurled.

Before the calyx breaks the size is medium, form moderately high pointed, the sepals are usually normal and regular, tapering to lanceolate at their apex, usually two with foliaceous appendages, those two also have a spur on each side thereof, turning back nearly perpendicular to the pedicel as the bud opens,usually no other spurs on sides.

Color of the bud as calyx opens, outside Straw Yellow at 604 splashed with Carmine at 21/1 to 21/3; color reference to English Horticultural Color Chart.[2]

*Bloom*

Outer petals gracefully recurled under normal environment.

Color outside of petals, outer rows colored and splashed as stated; inner petals, outer side, Straw Yellow at 604 shading toward base to Carrot Red at 612/1. Inner side

[1] This and other dates herein are approximate.

[2] Color references to same unless indicated.

of petals, Straw Yellow at 604 shading toward center of petal and to base to Shrimp Red at 616/2 and 616/1.

Color softens slowly to nearly Straw Yellow at 604/3.

Color slightly variable dependent upon quality of sun or other light.

The flower usually varies in size between 4 to 5 inches in diameter when fully open, petals average between 35 and 50, frequently some smaller petals and petaloids in the center, variable in number.

The flower opens moderately ovate and medium high centered, quite formal, with late display of stamens and pistils. The petals are variable from obovate to ovate to irregular and nearly formal as to arrangement and recurl, and edges of the smaller petals occasionally notably irregular. Texture is medium to thick; both sides brilliant. The time of opening in favorable conditions is about four days.

The petals are substantial and after about five days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

*Productive organs*

Stamens, quantity variable, medium long of slightly uneven length.

Anthers, nearly Marigold Orange at 11/3. Filaments, nearly Tangerine Orange at 9/3.

Pistils are several of nearly even length, averaging about one-half inch long.

Sepals are persistent and break off easily.

PLANT

*Foliage*

Is abundant, of compound leaves of three to five leaflets near the flower, five leaflets lower down the stem and frequently seven leaflets in the middle of the stems and nearer the base. Often with short narrow leafy formations variously positioned near the flower as shown. Size of leaflets medium. Form of leaflets usually nearly ovate with apex moderately acute, base rounded to slightly pointed in some instances with the circumference on one side of the petiolule out of alignment with the other side by about one-sixteenth of an inch or less, margins with slightly irregular small pointed serrations, petiolules medium short, and with slightly wider space than usual between leaflets.

The leaflets average in width about one-half of their length.

Color of leaflets on the upper surface is slightly variable from Spinach Green at o960, irregularly shaded with Parsley Green at oo962, with reverse side nearly Asphodel Green, the last color reference is to Robert Ridgway Color Standards.

The rachises are moderately narrow to slender, upper side smooth except some very short hairs almost microscopic on edges. Under side moderately smooth, usually three to five short prickles.

Stipules are long, averaging about ⅞ inch long or a little less, narrow with sharp point, the upper edges of which normally form an angle of about 90 degrees.

Plant habit, dwarf, becoming bushy to tall for a hybrid tea; upright, compact, more cumulative in growth from year to year than the normal hybrid tea rose plant, under favorable conditions up to five feet after two years, by stems from the base and by rebranching and growth and enlargement and extension of the stems from the base. The growth is moderately free at first, developing more rapidly after the first year under favorable vegetative opportunity.

Color of mature stems is Scheeles Green at 860/3, shading variously to nearly Parsley Green at oo962/2.

Prickles, several, frequently two to four between leaves, averaging in length about one-quarter to one-third inch, shading from Carmine at 21/2 to lighter at the base, turning lighter throughout and later to nearly colorless.

*Winter resistance*

A notable characteristic of this new rose is the resistance to moderate sub-zero temperatures in combination with its hybrid tea character, and its *Rosa wichuraiana* ancestry. The word temperature herein refers to the Fahrenheit scale.

*Comparisons*

The variety most nearly resembling my new rose is President Hoover, not patented, which lacks some of the hybrid tea type of rebloom expressed by my new rose.

My new rose has more petals, is more branching, blooms more, more constantly, and inherits from *Rosa Wichuraiana* more resistance to cold winters and to disease.

My new rose has a different fragrance.

I claim:

A new and distinct variety of rose plant, substantially as shown and described characterized by its color pattern, fragrance, form and color and its Wichuraiana traits.

No references cited.